(12) United States Patent
Safai

(10) Patent No.: US 10,541,102 B2
(45) Date of Patent: Jan. 21, 2020

(54) X-RAY BACK SCATTERING FOR INSPECTION OF PART

(71) Applicant: The Boeing Company, Chicago, IL (US)

(72) Inventor: Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 489 days.

(21) Appl. No.: 15/264,845

(22) Filed: Sep. 14, 2016

(65) Prior Publication Data

US 2018/0076000 A1 Mar. 15, 2018

(51) Int. Cl.
*G01N 15/02* (2006.01)
*H01J 35/14* (2006.01)
(Continued)

(52) U.S. Cl.
CPC .......... *H01J 35/14* (2013.01); *G01N 23/203* (2013.01); *H01J 35/065* (2013.01); *H01J 35/08* (2013.01); *H01J 35/16* (2013.01)

(58) Field of Classification Search
CPC .......... G01N 23/203; G01N 2223/053; G01N 23/04; G01N 23/20083; G01N 23/20; G01N 2223/301; G01N 2223/631; G01N 2223/303; G01N 23/20008; G01N 23/201; G01N 2223/419; G01N 2223/612; G01N 23/005; G01N 23/046; G21K 1/06; G21K 1/043; G21K 1/067; G21K 7/00; G21K 4/00; G21K 1/10; H01J 35/065; H01J 35/08; H01J 35/14; H01J 35/16;
(Continued)

(56) References Cited

U.S. PATENT DOCUMENTS

| | | | |
|---|---|---|---|
| 3,801,785 A | 4/1974 | Barrett | |
| 5,199,057 A * | 3/1993 | Tamura | G21K 7/00 378/43 |

(Continued)

OTHER PUBLICATIONS

Keskinbora et al., "Multilayer Fresnal zone plates for high energy radiation resolve 21 nm features at 1.2 keV," Optics Express, Jul. 28, 2014, pp. 18440-18453, vol. 22, No. 15, Optical Society of America.

(Continued)

*Primary Examiner* — Irakli Kiknadze
(74) *Attorney, Agent, or Firm* — Kunzler Bean & Adamson

(57) ABSTRACT

Described herein is an x-ray backscatter apparatus for non-destructive inspection of a part. The apparatus includes an x-ray emitter and a zone plate. The x-ray emitter includes an x-ray shield, a vacuum tube, a cathode, and an anode. The x-ray shield has an emission aperture. The vacuum tube is within the x-ray shield. The cathode and anode are enclosed within the vacuum tube. The cathode generates an electron emission. The anode is located relative to the cathode to receive the electron emission and convert the electron emission to a hard x-ray emission and is located relative to the emission aperture to direct at least a portion of the hard x-ray emission through the emission aperture. The zone plate is external to the x-ray shield and located relative to the emission aperture to receive the portion of the hard x-ray emission and focus the portion into a focused hard x-ray emission.

20 Claims, 9 Drawing Sheets

(51) Int. Cl.
*H01J 35/06* (2006.01)
*H01J 35/08* (2006.01)
*H01J 35/16* (2006.01)
*G01N 23/203* (2006.01)

(58) Field of Classification Search
CPC .......... H01J 35/02; H01J 35/101; H05G 1/02; H05G 1/60; G01J 3/02; G01J 3/4338; G01J 3/027; G01J 3/1895; G01J 3/0245; G01J 3/10; G01J 3/32; G01T 1/295; C09K 11/61; G01V 5/0025; A61B 6/06; A61B 6/548; A61B 6/581; A61B 6/583; A61B 6/4035; A61B 6/481; A61B 6/032; A61B 6/14; A61B 6/4064; A61B 6/4208; A61B 6/504; A61B 6/0435; A61B 6/483; A61B 6/502; A61B 6/487; A61B 6/542; A61B 6/12
USPC .............. 378/57, 70, 86–90, 138, 139, 145, 378/147–160
See application file for complete search history.

(56) References Cited

U.S. PATENT DOCUMENTS

| | | | |
|---|---|---|---|
| 6,128,364 A * | 10/2000 | Niemann | G21K 1/06 378/43 |
| 7,095,822 B1 * | 8/2006 | Yun | G01N 23/223 378/143 |
| 9,128,030 B1 | 9/2015 | Safai et al. | |
| 9,151,721 B2 | 10/2015 | Safai | |
| 9,305,344 B2 | 4/2016 | Georgeson et al. | |
| 9,543,109 B2 * | 1/2017 | Yun | H01J 35/106 |
| 2005/0105690 A1 * | 5/2005 | Pau | G21K 7/00 378/145 |
| 2007/0140423 A1 | 6/2007 | Foland | |
| 2007/0246655 A1 * | 10/2007 | Trissel | C09K 11/61 250/361 R |
| 2009/0052619 A1 * | 2/2009 | Endoh | G01N 23/04 378/43 |
| 2009/0072150 A1 * | 3/2009 | Trissel | C09K 11/61 250/363.01 |
| 2013/0129052 A1 * | 5/2013 | Toraya | G01N 23/207 378/71 |
| 2015/0192712 A1 * | 7/2015 | Jiang | G02B 5/1828 359/565 |

OTHER PUBLICATIONS

Gamaliy et al., The Use of Kumakhov Lenses in Diagnostics of Osteoporosis, SPIE, 2005, vol. 5943, pp. 202-209.
European Search Report for EP Patent Application No. 17173861 dated Nov. 21, 2017.

* cited by examiner

X-RAY BACK SCATTERING FOR INSPECTION OF PART

FIELD

This disclosure relates generally to the non-destructive inspection of parts, and more particularly to inspection of parts using x-ray backscatter apparatuses, systems, and methods.

BACKGROUND

Some inspection techniques, such as non-destructive testing, foreign object detection, non-line-of-site examination, etc., are employed when destruction of a part to be inspected is not desirable. Certain x-ray inspection techniques provide a penetrating scan or examination of a part. Such x-ray inspection techniques are used in a variety of applications, such as homeland security, oil and gas mining and refining, pipeline inspection, transportation, automotive, aerospace, marine, mining, shipping, and storage, among others.

Some inspection techniques utilize the detection of x-rays that pass through a part from one side of the part to the opposite side of the part. However, in other inspection techniques, such as x-ray backscattering techniques, the x-rays reflected back from the part (e.g., backscattered x-rays) are detected and then used to produce images or an analysis of the part. The pattern and intensity of the backscattered x-rays depends upon the materials and organization of the part. Accordingly, the pattern and intensity of the backscattered x-rays can be used to generate an image, which is relied upon to determine a quality, characteristic, or flaw of the part.

Traditionally, the quality of the image generated by x-ray backscattering techniques corresponds with the power density of the x-rays at the location where the x-rays impact the part to be inspected. For example, higher power densities generally lead to higher image quality. However, according to conventional techniques, an increase in the power density of x-rays at the point of impact with a part usually corresponds with an increase in potentially undesirable effects, such as an increase in heat generation, energy consumption, weight, and component and operating costs, among others.

SUMMARY

The subject matter of the present application has been developed in response to the present state of the art, and in particular, in response to the shortcomings of traditional x-ray backscatter devices, that have not yet been fully solved by currently available techniques. Accordingly, the subject matter of the present application has been developed to provide a backscatter device, and associated apparatuses, systems, and methods, with a zone plate, that overcomes at least some of the above-discussed shortcomings of prior art techniques.

Disclosed herein is an x-ray backscatter apparatus for non-destructive inspection of a part. The apparatus includes an x-ray emitter and a zone plate. The x-ray emitter includes an x-ray shield, a vacuum tube, a cathode, and an anode. The x-ray shield has an emission aperture. The vacuum tube is within the x-ray shield. The cathode is enclosed within the vacuum tube and is selectively operable to generate an electron emission. The anode is enclosed within the vacuum tube and located relative to the cathode to receive the electron emission and convert the electron emission from the cathode to a hard x-ray stream. In one embodiment, an x-ray stream is defined as a hard x-ray stream if the x-rays of the stream have an energy level greater than 5-10 keV. In another embodiment, the x-ray stream is a hard x-ray stream if it has an energy level above 50 keV. In a further embodiment, the x-ray stream is a hard x-ray stream if the x-rays of the stream have an energy level between approximately 60 keV and approximately 80 keV. In other embodiments, the hard x-ray stream includes x-rays having an energy level greater than 80 keV. The anode is located relative to the emission aperture to direct at least a portion of the hard x-ray stream through the emission aperture. The zone plate is external to the x-ray shield and located relative to the emission aperture. The zone plate receives the portion of the hard x-ray stream from the emission aperture of the x-ray shield and focuses the portion of the hard x-ray stream received from the emission aperture into a focused hard x-ray stream. The preceding subject matter of this paragraph characterizes example 1 of the present disclosure.

The zone plate includes a plurality of Fresnel zones. The preceding subject matter of this paragraph characterizes example 2 of the present disclosure, wherein example 2 also includes the subject matter according to example 1, above.

At least one of the plurality of Fresnel zones of the zone plate has at least one radius corresponding to a focal length of the zone plate. The preceding subject matter of this paragraph characterizes example 3 of the present disclosure, wherein example 3 also includes the subject matter according to any one of examples 1 or 2, above.

The zone plate is made, at least partially, of carbon nanotubes. The preceding subject matter of this paragraph characterizes example 4 of the present disclosure, wherein example 4 also includes the subject matter according to any one of examples 1-3, above.

The zone plate is made, at least partially, of lead. The preceding subject matter of this paragraph characterizes example 5 of the present disclosure, wherein example 5 also includes the subject matter according to any one of examples 1-4, above.

The zone plate comprises a surface plating. The preceding subject matter of this paragraph characterizes example 6 of the present disclosure, wherein example 6 also includes the subject matter according to any one of examples 1-5, above.

The surface plating is gold. The preceding subject matter of this paragraph characterizes example 7 of the present disclosure, wherein example 7 also includes the subject matter according to any one of examples 1-6, above.

The hard x-ray stream has an energy level between approximately 60 keV and approximately 80 keV. The preceding subject matter of this paragraph characterizes example 8 of the present disclosure, wherein example 8 also includes the subject matter according to any one of examples 1-7, above.

Also disclosed herein is an x-ray backscatter system for non-destructive inspection of a part. The system includes a base, an x-ray emitter, an inspection filter, and a zone plate. The x-ray emitter is coupled to the base. The inspection filter is movable coupled to the base and selectively operable to receive a hard w-ray emission from the x-ray emitter and pass at least a portion of the hard x-ray emission through a filter aperture in the inspection filter to a selectable location on the part. The zone plate is interposed between the x-ray emitter and the inspection filter. The zone plate receives the hard x-ray emission from the x-ray emitter and modifies a beam pattern of the hard x-ray emission received from the x-ray emitter. The preceding subject matter of this paragraph characterizes example 9 of the present disclosure.

The system further includes a detector coupled to the base and selectively operable to detect hard x-rays backscattered from the part. The preceding subject matter of this paragraph characterizes example 10 of the present disclosure, wherein example 10 also includes the subject matter according to example 9, above.

The zone plate is moveable relative to the x-ray emitter to further modify the beam pattern of the hard x-ray emission received from the x-ray emitter. The preceding subject matter of this paragraph characterizes example 11 of the present disclosure, wherein example 11 also includes the subject matter according to any one of examples 9 or 10, above.

The x-ray emitter and the zone plate are adjustable relative to the base to modify an emission direction relative to the base. The preceding subject matter of this paragraph characterizes example 12 of the present disclosure, wherein example 12 also includes the subject matter according to any one of examples 9-11, above.

The base includes a mobility system operable to move the base relative to the part. The preceding subject matter of this paragraph characterizes example 13 of the present disclosure, wherein example 13 also includes the subject matter according to any one of examples 9-12, above.

The mobility system includes at least one of a wheel, a tread, a skid, a track, a roller, a cable, a pulley, a motor, a slide, and a beating. The preceding subject matter of this paragraph characterizes example 14 of the present disclosure, wherein example 14 also includes the subject matter according to any one of examples 9-13, above.

The system further includes a control unit to control a position of the zone plate relative to the x-ray emitter or relative to the inspection filter. The preceding subject matter of this paragraph characterizes example 15 of the present disclosure, wherein example 15 also includes the subject matter according to any one of examples 9-14, above.

The inspection filter includes a rotatable ring with a plurality of apertures. At least one of the plurality of apertures is different from another of the plurality of apertures. The preceding subject matter of this paragraph characterizes example 16 of the present disclosure, wherein example 16 also includes the subject matter according to any one of examples 9-15, above.

Also disclosed herein is a method of non-destructive inspection of a part by x-ray backscatter. The method includes receiving a hard x-ray emission from an x-ray emitter at a zone plate. The method also includes focusing the hard x-ray emission into a focused hard x-ray stream with the zone plate. The method also includes directing at least a portion of the focused hard x-ray stream with the zone plate through a first filter aperture of an inspection filter and onto a first portion of the part. The preceding subject matter of this paragraph characterizes example 17 of the present disclosure.

The method further includes adjust an orientation of the inspection filter relative to the zone plate such that the focused hard x-ray stream is directed through a second filter aperture of the inspection filter and onto a second portion of the part. The second filter aperture is different from the first filter aperture. The preceding subject matter of this paragraph characterizes example 18 of the present disclosure, wherein example 18 also includes the subject matter according to example 17, above.

Focusing the hard x-ray emission includes focusing the hard x-ray emission by between approximately 30% and approximately 40%. The preceding subject matter of this paragraph characterizes example 19 of the present disclosure, wherein example 19 also includes the subject matter according to any one of examples 17 and 18, above.

The portion of the focused hard x-ray stream directed through the first filter aperture constitutes between approximately 60% and approximately 70% of the hard x-ray emission from the x-ray emitter. The preceding subject matter of this paragraph characterizes example 20 of the present disclosure, wherein example 20 also includes the subject matter according to any one of examples 17-19, above.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

Figure 1A:
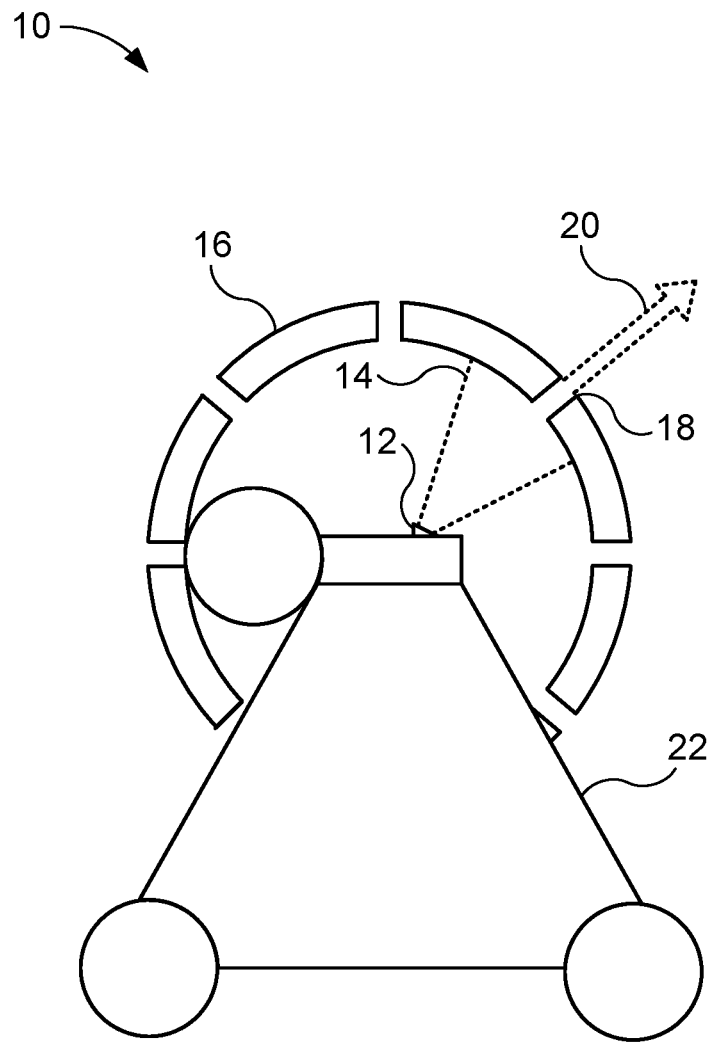
FIG. 1A is a schematic view of an x-ray backscatter apparatus, according to one or more embodiments of the present disclosure.

Referring to FIG. 1A, an x-ray backscatter apparatus 10 is shown. The x-ray backscatter apparatus 10 includes an x-ray emitter 12 to produce an incident x-ray emission 14, an inspection filter 16, with a plurality of filter apertures 18 to produce a filtered x-ray emission 20, and a base 22.

The x-ray emitter 12 is coupled to the base 22. The x-ray emitter 12 generates the incident x-ray emission 14 and projects the incident x-ray emission 14 onto the inspection filter 16 proximate a filter aperture 18. Only a portion (i.e., the filtered x-ray emission 20) of the incident x-ray emission 14 passes through the filter aperture 18. The filtered x-ray emission 20 is then used to inspect a part or other target. As shown in the depicted embodiment, the filtered x-ray emission 20 is a relatively small percentage of the incident x-ray emission 14 generated by the x-ray emitter 12. As such, the power density of the filtered x-ray emission 20, which is the power density of the x-rays impacting the part and available for inspection of the part, is less than the power density of the incident x-ray emission 14. Accordingly, in some cases, the majority of the incident x-ray emission 14 generated by the x-ray emitter 12 is lost at the inspection filter 16. To compensate for the loss of power density, in some cases, the x-ray emitter 12 generates an incident x-ray emission 14 with a power density that is much greater than is required at the part, which contributes to reduced efficiency.

Figure 1B:
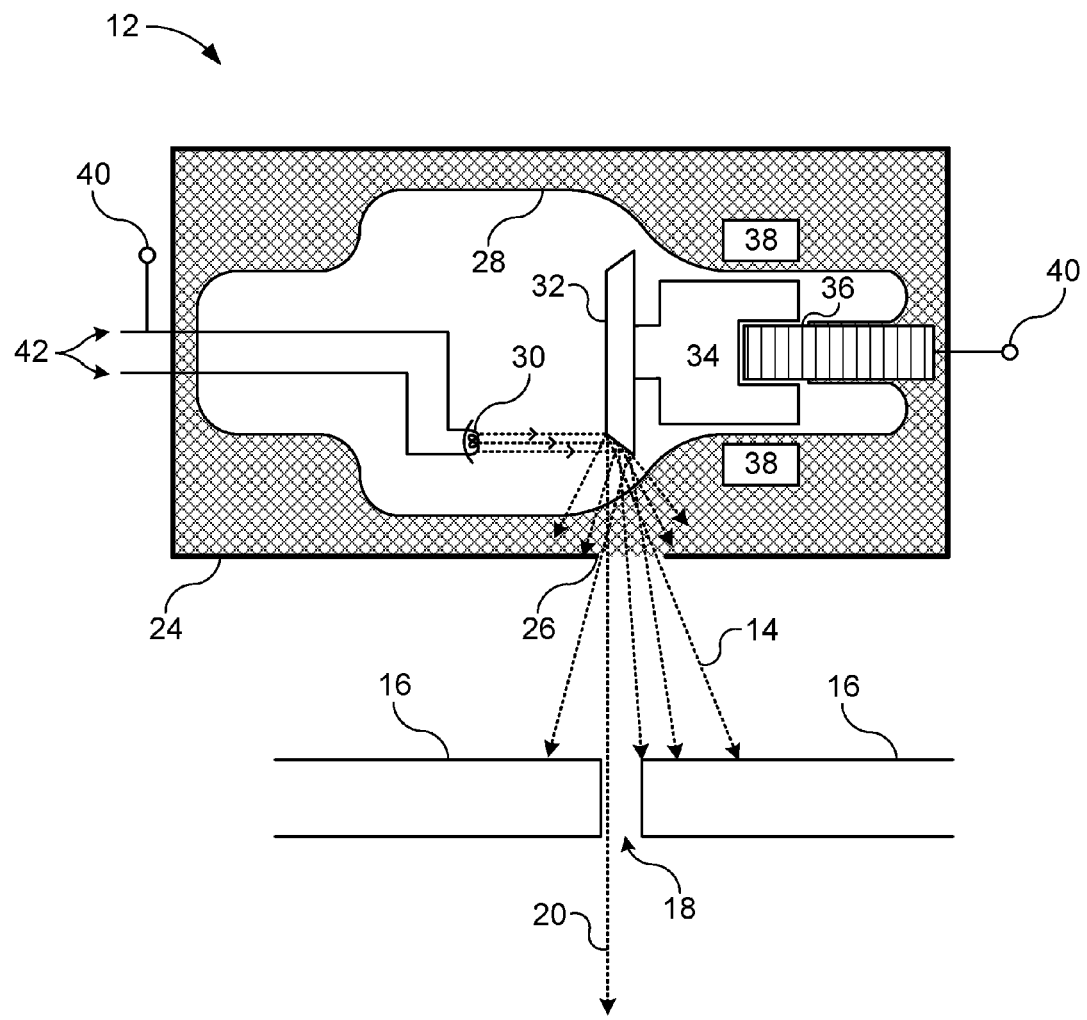
FIG. 1B is a schematic view of an x-ray emitter of the x-ray backscatter apparatus of FIG. 1A, according to one or more embodiment of the present disclosure.

FIG. 1B illustrates an x-ray emitter 12 of the x-ray backscatter apparatus 10 of FIG. 1A. The x-ray emitter 12 includes an x-ray shield 24. Moreover, the x-ray shield 24 includes an emission aperture 26. The x-ray shield 24, with the exception of the emission aperture 26, encloses a vacuum tube 28. The vacuum tube 28 encloses a cathode 30 and an anode 32. The cathode 30 and anode 32 are connected to a voltage supply via leads 40. The cathode 30 is further connected to a filament supply line 42 and is selectively operable to generate an electron emission that is received at the anode 32. The anode 32 receives the electron emission, from the cathode 30, and generates a hard x-ray stream. The hard x-ray stream is directed towards the emission aperture 26 of the x-ray shield 24. A portion of the hard x-ray stream from the anode 32 passes through the emission aperture 26 while a separate portion of the hard x-ray stream is blocked by the x-ray shield 24. The portion of the hard x-ray stream that passes through the emission aperture 26 is the incident x-ray emission 14.

In the illustrated representation, the anode 32 of the x-ray emitter 12 is a rotating anode. However, in other representations, the anode 32 of the x-ray emitter 12 does not rotate. The anode 32 can be a tungsten anode coupled to a rotor 34. The rotor 34 is supported by a rotor support 36 and can be coupled to the rotor support 36 with bearings or other structures that facilitate relative rotation between the rotor 34 and the rotor support 36. The rotor 34 is driven by a motor 38. A magnetic field created by applying an electrical signal to the motor 38 applies a force to the rotor 34 to turn the rotor 34 and the anode 32.

In the illustrated embodiment, the incident x-ray emission 14 then reaches the inspection filter 16 as described in associated FIG. 1A. Due to the relatively unfocused nature of the incident x-ray emission 14 and the relatively small size of the filter aperture 18, only a portion of the incident x-ray emission 14 that reaches the inspection filter 16 passes through the filter aperture 18. In other words, the portion of the incident x-ray emission 14 that passes through the filter aperture 18 (i.e., the filtered x-ray emission 20) is small relative to the incident x-ray emission 14 and even smaller compared to the x-rays generated by the anode 32 before exiting the emission aperture 26.

Figure 2A:
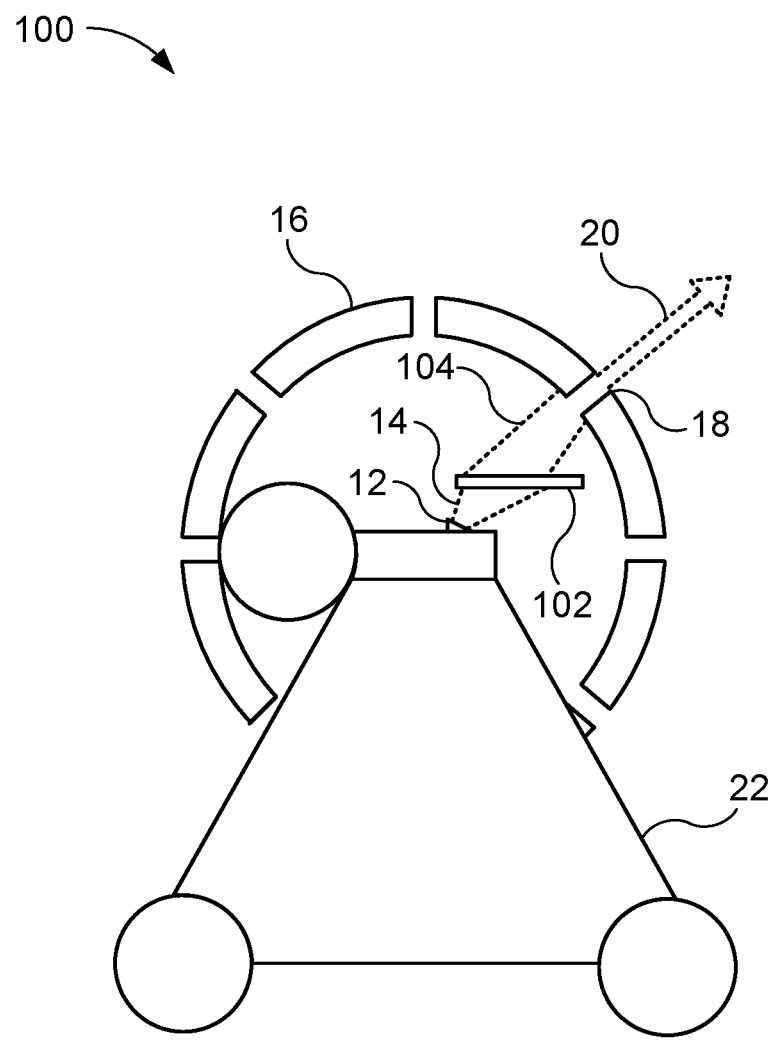
FIG. 2A is a schematic cross-sectional side view of an x-ray backscatter apparatus, according to one or more embodiments of the present disclosure.

FIG. 2A is a schematic cross-sectional view of an x-ray backscatter apparatus 100. The x-ray backscatter apparatus 100 includes features analogous to features of the x-ray backscatter system 10 of FIG. 1A, with like numbers referring to like features. However, the x-ray backscatter apparatus 100 of FIG. 2A provides advantages over the x-ray backscatter system 10 of FIG. 1A. For example, the x-ray backscatter apparatus 100 includes a zone plate 102 interposed between the x-ray emitter 12 and the filter aperture 18 of the inspection filter 16. Generally, the zone plate 102 receives the incident x-ray emission 14 from the x-ray emitter 12 and focuses the incident x-ray emission 14 into a focused x-ray emission 104. The focused x-ray emission 104 is directed, by the zone plate 102, toward the filter aperture 18 of the inspection filter 16. A portion of the focused x-ray emission 104 passes through the filter aperture 18 to define the filtered x-ray emission 20. By first focusing the incident x-ray emission 14 into a focused x-ray emission 104, before passing through the filter aperture 18 of the inspection filter 16, a higher amount or concentration of x-rays, and thus a higher power density of x-rays, passes through the filter aperture 18 and impacts the part to be inspected. Accordingly, the portion of the incident x-ray emission 14 converted into the filtered x-ray emission 20 is greater with the x-ray backscatter apparatus 100, because of the zone plate 102, than with the x-ray backscatter apparatus 10.

Therefore, to achieve the same power density of the filtered x-ray emission 20, the x-ray backscatter apparatus 100 can generate an incident x-ray emission 14 with a lower energy density compared with the x-ray backscatter system 10, which promotes certain advantages. For example, the x-ray backscatter apparatus 100 promotes one or more of a wider area of x-ray imaging, a larger field of view, a larger inspection angle, an improved image resolution, an improved image sharpness, a reduced number of required transverse scans, a dynamic and instantaneous field of view, a reduced image distortion, a reduced pin-cushion effect at imaging corners, a reduced power supply requirement, a reduced cooling requirement, a reduced system weight, a reduced system size, an improved portability, an improved viability for a broader range of testing situations, and an improved component life compared with the x-ray backscatter apparatus 10.

As used herein, the focused x-ray emission 104 may include any x-ray emission or stream in which at least a portion of the x-rays of the focused x-ray emission 104 are modified by the zone plate 102 to be less divergent than the x-rays of the incident x-ray emission 14 from the x-ray emitter 12. The focused x-ray emission 104 may also include any x-ray stream in which a portion of the x-rays of the focused x-ray emission 104 are modified to a convergent mode from a divergent mode by the zone plate 102. The zone plate 102 may also modify the received x-rays from a divergent mode to a collimated mode. In some examples, the zone plate 102 may receive the incident x-ray emission 14 in a mode that is at least partially convergent and further focus the x-rays to greater convergence. Alternatively, the zone plate 102 may receive the incident x-ray emission 14 in a divergent mode and focus the incident x-ray emission 14 into a less divergent state.

In some examples, the zone plate 102 may provide between approximately 20% and approximately 40% focus of the received x-rays. More specifically, the zone plate 102 may provide approximately 30% focus. Other embodiments of the zone plate 102 may focus more or less than the examples given above. In some embodiments, the zone plate 102 may focus the incident x-ray emission 14 sufficient to pass between approximately 60% and approximately 70% of the incident x-ray emission 14 through the filter aperture 18 as the focused x-ray emission 104.

In some implementations, the zone plate 102 may be made wholly or partially of lead. In some embodiments, the density of the lead allows for a greater effect of the zone plate 102 on the incident x-ray emission 14. In some embodiments, the zone plate 102 may include carbon nanotubes. Carbon nanotubes offer benefits in weight reduction, thermal conduction and cooling, and strength. The zone plate 102 may also include a surface treatment. The surface treatment may include plating, doping, hardening, coating, or some other chemical, mechanical, or thermal treatment.

The zone plate 102 may be positioned to receive some or all of the incident x-ray emission 14 from the x-ray emitter 12. In the illustrated embodiment, the zone plate 102 is shown in a horizontal orientation. However, the zone plate 102 may be oriented at a zero or non-zero orientation from horizontal. In some embodiments, the zone plate 102 may be oriented at a zero or non-zero angle relative to the x-ray emitter 12, relative to the filter aperture 18, relative to the base 22, or relative to some other physical or construct point of reference on or outside of the x-ray backscatter apparatus 100. In some embodiments, the position and orientation of the zone plate 102 is adjustable. The adjustability of the zone plate 102 is facilitated by a frame or other mounting structure (not shown) to which the zone plate 102 is coupled. In other embodiments, the zone plate 102 is coupled to a cooling system to cool the zone plate 102 through conduction, convection, or radiation.

While the illustrated embodiment depicts the zone plate 102 as located outside of the x-ray emitter 12, in other embodiments, the zone plate 102 is incorporated into the x-ray emitter 12 as a unified portion of the x-ray emitter 12. In an alternative embodiment, multiple zone plates 102 are coupled to the inspection filter 16 to correspond with each filter aperture 18 individually or so that each zone plate 102 corresponds to multiple filter apertures 18 on the inspection filter 16.

Figure 2B:
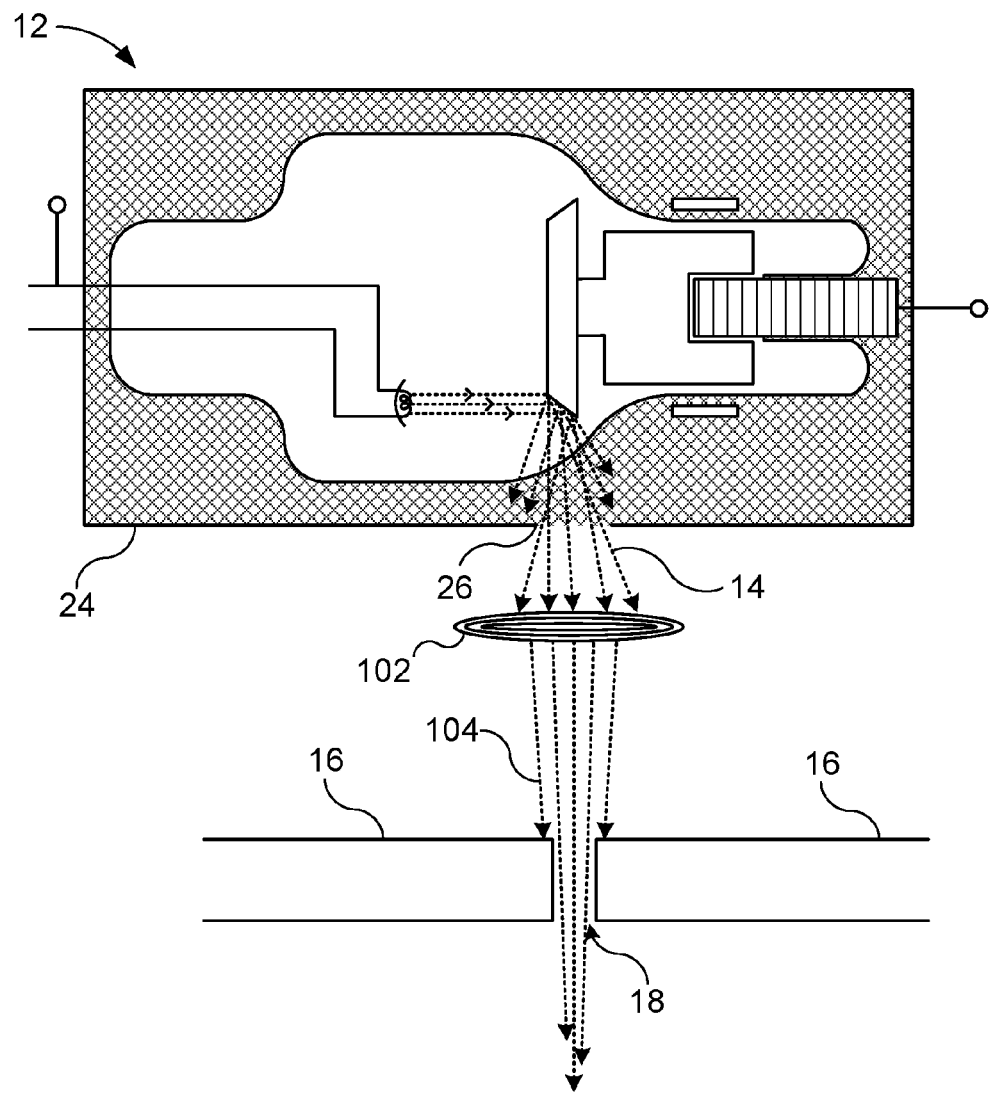
FIG. 2B is a schematic cross-sectional side view of an x-ray emitter of the x-ray backscatter apparatus of FIG. 2A, according to one or more embodiments of the present disclosure.

Referring to FIG. 2B, the zone plate 102 of FIG. 2A is shown relative to the x-ray emitter 12 of FIG. 1B. In the illustrated embodiment, the zone plate 102 is located relative to the emission aperture 26 of the x-ray emitter 12. In this arrangement, the zone plate 102 receives at least a portion of the incident x-ray emission 14 passing through the emission aperture 26. In some embodiments, the zone plate 102 is coaxial with the emission aperture 26 or is oriented at some other angle. In an alternative embodiment, the zone plate 102 is coaxial with the filter aperture 18. In the illustrated embodiment, the zone plate 102 is shown between the x-ray emitter 12 and the inspection filter 16. In some embodiments, the zone plate 102 is positioned closer to the x-ray emitter 12 or closer to the inspection filter 16. In other embodiments, the zone plate 102 is positioned equidistant from the x-ray emitter 12 and the inspection filter 16. In some implementations, the position of the zone plate 102 is adjustable relative to at least one of the x-ray emitter 12 and the inspection filter 16. In some embodiments, the zone plate 102 rotates to direct the focused x-ray emission 104 to the filter aperture 18 as the inspection filter 16 is translated or rotated relative to the x-ray emitter 12.

Figure 2C:
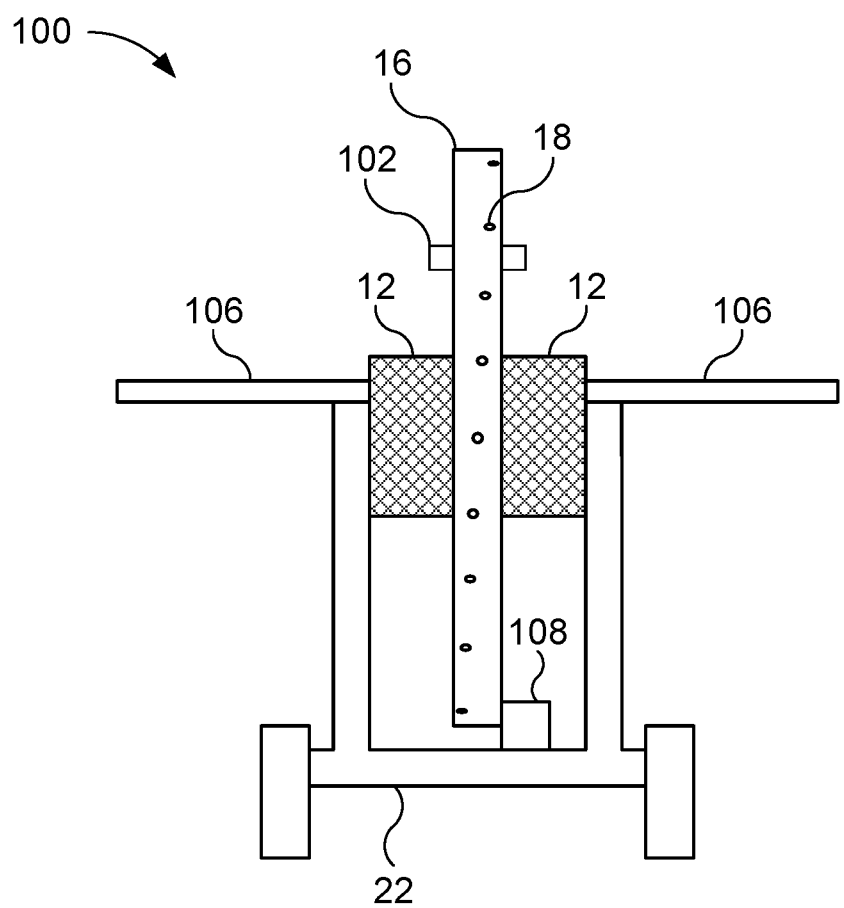
FIG. 2C is a schematic side view of the x-ray backscatter apparatus of FIG. 2A, according to one or more embodiments of the present disclosure.

FIG. 2C is a schematic side view of the x-ray backscatter apparatus 100 of FIG. 2A. The illustrated embodiment includes detectors 106 coupled to the base 22. The detectors 106 are positioned to receive backscattered x-rays from a part during inspection. Two detectors 106 are shown. In some alternative embodiments, the x-ray backscatter apparatus 100 includes fewer or more than two detectors 106. For example, the x-ray backscatter apparatus 100 may include a single detector 106 positioned in front of an outer edge of the inspection filter 16 so as to be near an impact point of the x-rays at a part. Alternatively, the x-ray backscatter apparatus 100 includes three or more detectors 106 to collect additional backscattered x-rays to make a more complete and clear image of the part. In an exemplary embodiment, the detectors 106 are shielded from x-rays that are reflected or refracted from the x-ray emitter 12, the zone plate 102, the inspection filter 16, and/or the filter apertures 18. In one embodiment, the detectors 106 are fixed while in other embodiments, the detectors 106 are adjustable relative to the base 22 in order to improve the detection of backscattered x-rays, to reduce image noise from non-backscattered x-rays, or accommodate an inspection constraint. In an additional embodiment, once an optimal position of the detectors 106 is determined, the detectors 106 may be fixed relative to the base 22.

In the depicted implementation, the zone plate 102 is located between the x-ray emitter 12 and an inner surface of the inspection filter 16. The zone plate 102 remains in place as the inspection filter 16 rotates around the x-ray emitter 12. The inspection filter 16 position is controlled by a motor 108 coupled to the inspection filter 16. As described above, some embodiments include multiple zone plates 102 coupled to the inspection filter 16 at different points along the inside of the inspection filter 16. The placement of each of the multiple zone plates 102 corresponds to the location of one or more of the filter apertures 18.

In the depicted embodiment, the filter apertures 18 are placed at consistent intervals along a perimeter of the inspection filter 16 with each filter aperture 18 at a different distance from the edge of the inspection filter 16. In some embodiments, the filter apertures 18 are uniform while in other embodiments, the filter apertures 18 vary by location, spatial frequency, size, shape, geometry, material (or lack thereof), or other characteristics. In some implementations, the zone plate 102 is positioned based on the characteristics of the filter aperture 18 positioned to receive the focused x-ray emission from the zone plate 102. In other implementations, the zone plate 102 is fixed but configured to produce a focused x-ray emission sufficient for each of the filter apertures 18.

Figure 3:
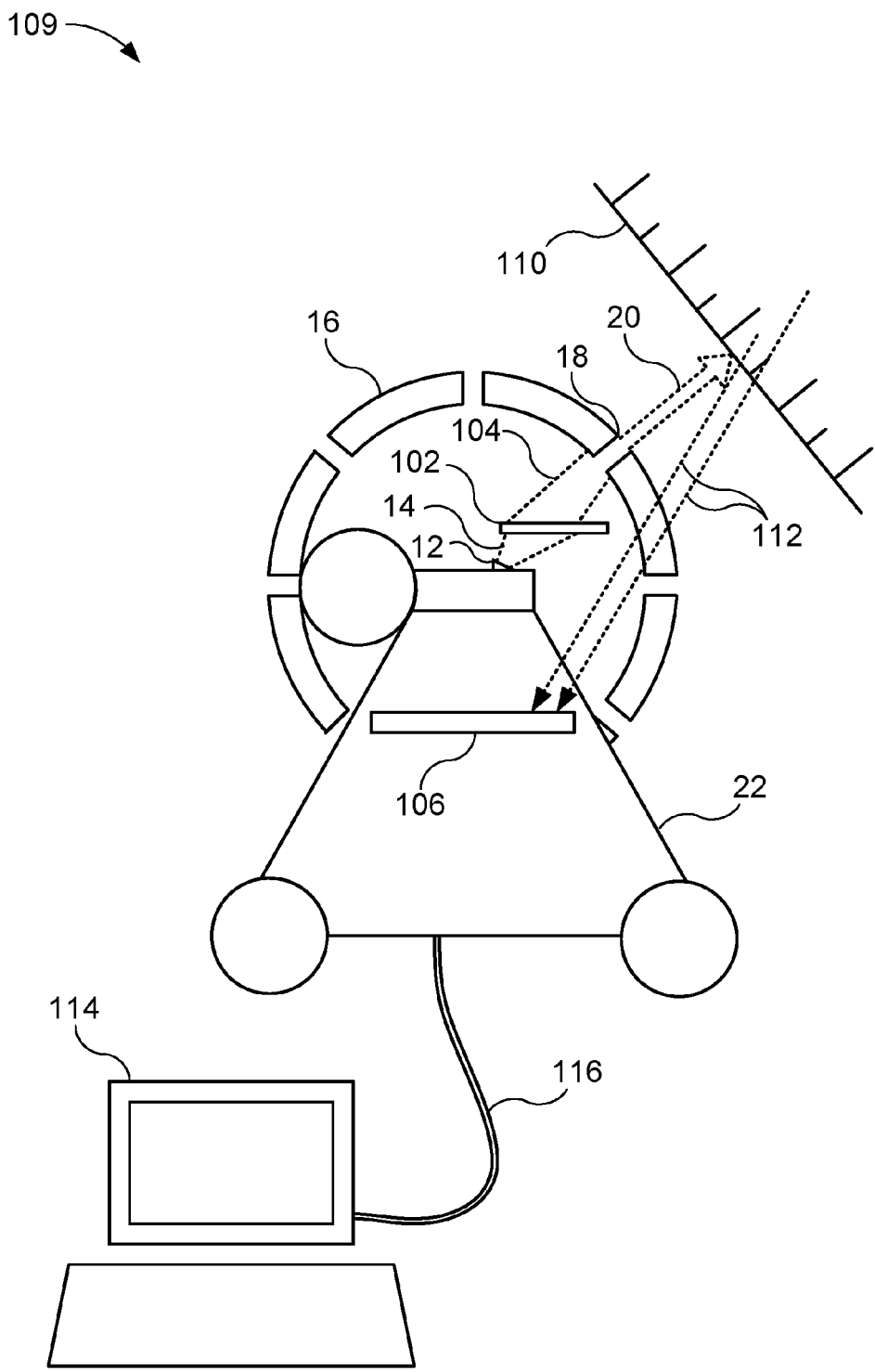
FIG. 3 is a schematic side view of an x-ray backscatter system, according to one or more embodiments of the present disclosure.

FIG. 3 illustrates a schematic view of an x-ray backscatter system 109. In the depicted implementation, the x-ray backscatter system 109 is positioned to inspect a part 110. In particular, the x-ray emitter 12 generates an incident x-ray emission 14 which is received by the zone plate 102. The zone plate 102 modifies a beam pattern of the incident x-ray emission 14 to generate the focused x-ray emission 104. The focused x-ray emission 104 impinges on the inspection filter 16 at approximately the filter aperture 18. The filter aperture 18 filters the focused x-ray emission 104 to pass a portion of the focused x-ray emission 104. In some embodiments, the filtered x-ray emission 20 has a particular pattern or characteristic applied by the filter aperture 18 at the part 110 to facilitate inspection. The filtered x-ray emission 20 that passes through the filter aperture 18 reaches the part 110 and some x-rays are backscattered towards the detector 106. Some of the backscattered x-rays 112 are detected by the detector 106. A signal, which corresponds with the detected backscattered x-rays 112, is sent from the detector 106 to a control system 114. In some implementations, the inspection filter 16 may be rotated so that a different portion of the part 110 receives and backscatters the x-rays. Additional signals are generated at the detector 106 and sent to the control system 114.

In some embodiments, the control system 114 interprets the signals to generate an image or other inspection results. In some embodiments, the control system 114 also provides signals to control the generation of x-rays by the x-ray emitter 12, movement of the inspection filter 16, movement of the base 22 relative to the part 110, movement of the zone plate 102, control of a cooling system or power source, or monitoring of a system or individual component state via sensors or other devices. The control system 114 includes a connection 116 to the x-ray backscatter system 109. The connection 116 may be a wired or wireless connection. In the depicted implementation, the control system 114 is separate from the x-ray backscatter system 109. Alternatively, the control system 114 is coupled to the base 22 or otherwise integrated into the x-ray backscatter system 109.

Figure 4:
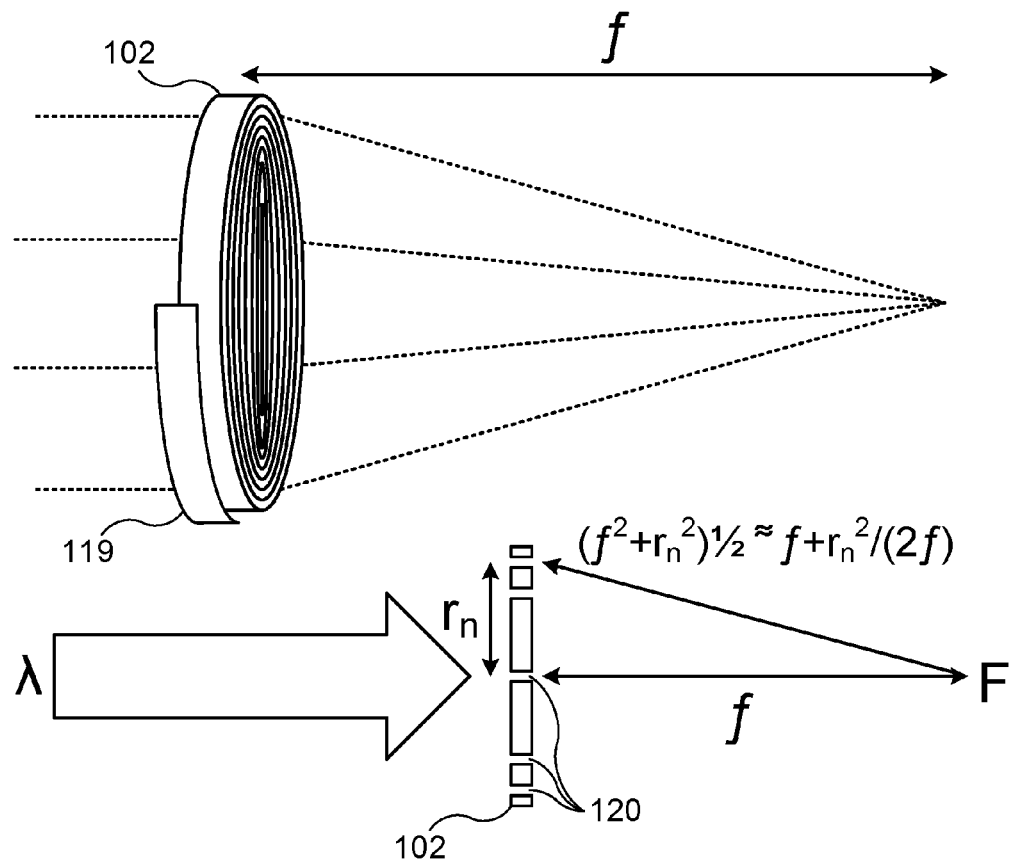
FIG. 4 is a perspective view and a cross-sectional side view of a zone plate, according to one or more embodiments of the present disclosure.

FIG. 4 shows a perspective view and a cross-sectional side view of a zone plate 102. In the illustrated embodiment, the zone plate 102 has a focal length f. Given a particular focal length f for a system (distance from the zone plate 102 to the filter aperture 18 or part 110 of FIG. 3), a radius characteristic of the zone plate 102 may be determined. In some embodiments, the zone plate 102 includes a surface treatment 119. The surface treatment 119 may include plating, doping, hardening, coating, or some other chemical, mechanical, or thermal treatment. In one example, the surface treatment 119 includes a gold plating.

Similarly, in the case of a Fresnel zone plate 102, the radii, and corresponding spacing, of the plurality of Fresnel zones 120 in the Fresnel zone plate 102 may be determined. In some implementations, the focal length f corresponds with the focal point F of each of the plurality of Fresnel zones 120. In other implementations, the Fresnel zones 120 may be configured to have different focal lengths f or focal points F to facilitate inspection at a range of depths within a part.

Figure 5:
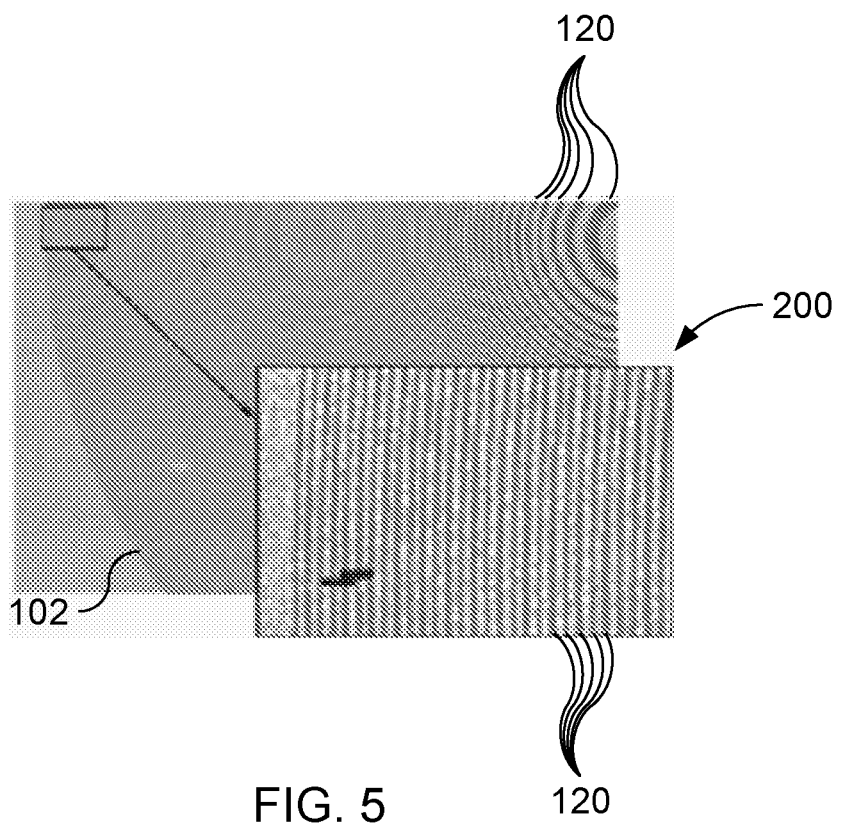
FIG. 5 is a scanning electron microscope micrograph of a zone plate, according to one or more embodiments of the present disclosure.

FIG. 5 is a scanning electron microscope micrograph 200 of a zone plate 102. The micrograph 200 illustrates the plurality of Fresnel zones 120. The micrograph 200 depicts a 25 nm section of the outmost portion of a zone plate 102. In this example, the diameter of the zone plate 102 is 63 mm with 628 Fresnel zones 120 and gold plating over lead. In other examples, the zone plate 102 may include fewer or more Fresnel zones, a greater or lesser diameter, and other or no plating materials or surface treatments.

Figure 6:
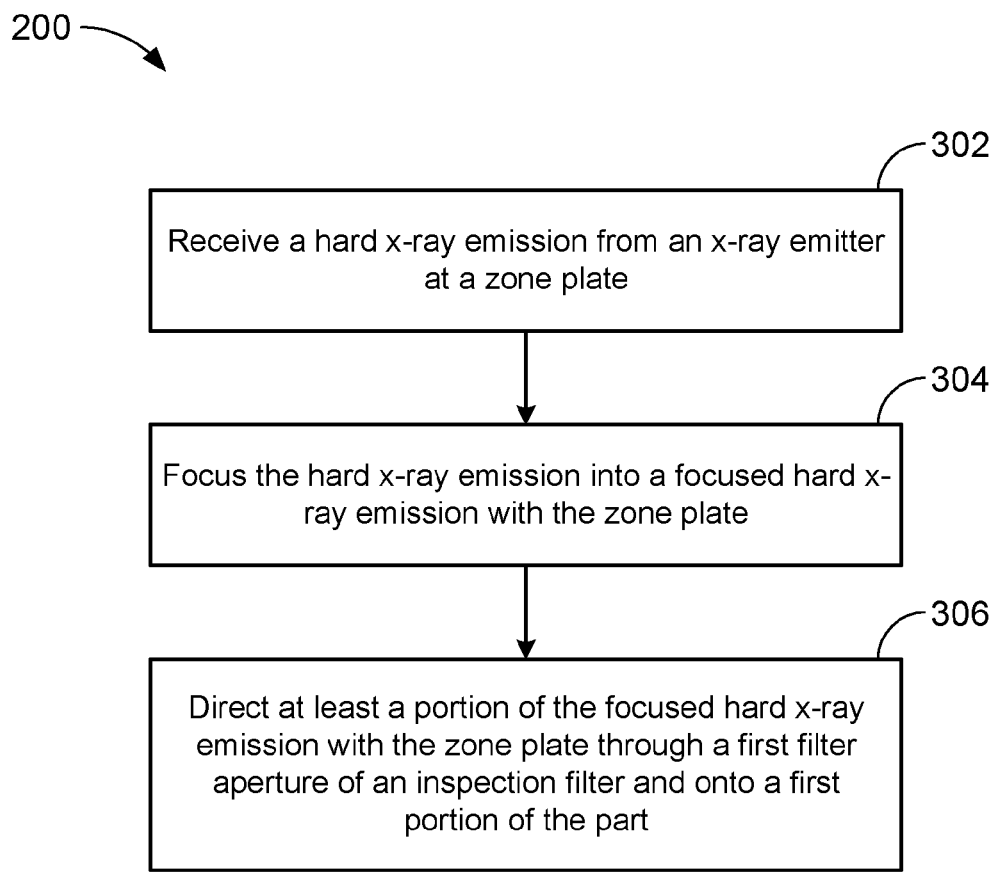
FIG. 6 is a schematic flow diagram of a method of non-destructive inspection of a part by x-ray backscatter, according to one or more embodiments of the present disclosure.

Referring to FIG. 6, a method 300 of non-destructive inspection of a part by x-ray backscatter is shown. The method 300 includes receiving a hard x-ray emission from an x-ray emitter at a zone plate, at 302. Additionally, the method 300 includes focusing the hard x-ray emission into a focused hard x-ray emission with the zone plate, at 304. The method 300 further includes, directing at least a portion of the focused hard x-ray emission with the zone plate through a first filter aperture of an inspection filter and onto a first portion of the part, at 306.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of," when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enables the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. An x-ray backscatter apparatus for non-destructive inspection of a part, the apparatus comprising:
    an x-ray emitter, comprising:
        an x-ray shield, comprising an emission aperture;
        a vacuum tube within the x-ray shield;
        a cathode enclosed within the vacuum tube and selectively operable to generate an electron emission; and
        an anode, enclosed within the vacuum tube and located relative to the cathode, to receive the electron emission and convert the electron emission from the cathode to a hard x-ray emission, and located relative to the emission aperture to direct at least a portion of the hard x-ray emission through the emission aperture;
    an inspection filter, separate from the x-ray emitter; and
    a zone plate, external to the x-ray shield and located relative to the emission aperture, to receive the portion of the hard x-ray emission from the emission aperture of the x-ray shield and to focus the portion of the hard x-ray emission received from the emission aperture into a focused hard x-ray emission, wherein the zone plate is fixed relative to the x-ray emitter and is positioned between the x-ray emitter and the inspection filter to direct the focused hard x-ray emission to the inspection filter, the inspection filter being rotatable relative to the zone plate to pass a portion of the focused hard x-ray emission based on a rotational position of the inspection filter relative to the zone plate.

2. The apparatus according to claim 1, wherein the zone plate comprises a plurality of Fresnel zones.

3. The apparatus according to claim 2, wherein at least one of the plurality of Fresnel zones of the zone plate has at least one radius corresponding to a focal length of the zone plate.

4. The apparatus according to claim 1, wherein the zone plate is made, at least partially, of carbon nanotubes.

5. The apparatus according to claim 1, wherein the zone plate is made, at least partially, of lead.

6. The apparatus according to claim 1, wherein the zone plate comprises a surface treatment.

7. The apparatus according to claim 6, wherein the surface treatment is a gold plating.

8. The apparatus according to claim 1, wherein the hard x-ray stream has an energy level between approximately 60 keV and approximately 80 keV.

9. An x-ray backscatter system for non-destructive inspection of a part, the system comprising:
    a base;
    an x-ray emitter coupled to the base;
    an inspection filter movably coupled to the base and rotatably positionable to receive a hard x-ray emission from the x-ray emitter and pass at least a portion of the hard x-ray emission through a filter aperture in the inspection filter to a selectable location on the part based on a rotational position of the inspection filter relative to the x-ray emitter; and
    a zone plate, interposed between the x-ray emitter and the inspection filter, to receive the hard x-ray emission from the x-ray emitter, modify a beam pattern of the hard x-ray emission received from the x-ray emitter into a modified beam pattern, and pass the modified beam pattern of the hard x-ray emission to the inspection filter.

10. The system according to claim 9, further comprising a detector coupled to the base and selectively operable to detect hard x-rays backscattered from the part.

11. The system according to claim 9, wherein the zone plate is moveable relative to the x-ray emitter to further modify the beam pattern of the hard x-ray emission received from the x-ray emitter.

12. The system according to claim 9, wherein the x-ray emitter and the zone plate are adjustable relative to the base to modify an emission direction relative to the base.

13. The system according to claim 9, wherein the base comprises a mobility system operable to move the base relative to the part.

14. The system according to claim 13, wherein the mobility system comprises at least one of a group, the group consisting of a wheel, a tread, a skid, a track, a roller, a cable, a pulley, a magnet, a motor, a slide, and a bearing.

15. The system according to claim 9, further comprising a control unit to control a position of the zone plate relative to the x-ray emitter or relative to the inspection filter.

16. The system according to claim 9, wherein the inspection filter comprises a rotatable ring with a plurality of apertures, wherein at least one of the plurality of apertures is different from another of the plurality of apertures.

17. A method of non-destructive inspection of a part by x-ray backscatter, the method comprising:
    receiving a hard x-ray emission from an x-ray emitter at a zone plate;
    focusing the hard x-ray emission into a focused hard x-ray emission with the zone plate; and
    directing at least a portion of the focused hard x-ray emission with the zone plate through a first filter aperture of an inspection filter and onto a first portion of the part corresponding to a rotational position of the inspection filter relative to the zone plate, wherein the zone plate is positioned between the x-ray emitter and the inspection filter.

18. The method according to claim 17, further comprising adjusting an orientation of the inspection filter relative to the zone plate such that the focused hard x-ray emission is directed through a second filter aperture of the inspection filter and onto a second portion of the part, wherein the second filter aperture is different from the first filter aperture.

19. The method according to claim 17, wherein focusing the hard x-ray emission comprises focusing the hard x-ray emission by between approximately 30% and approximately 40%.

20. The method according to claim 17, wherein the portion of the focused hard x-ray emission directed through the first filter aperture constitutes between approximately 60% and approximately 70% of the hard x-ray emission from the x-ray emitter.

* * * * *